United States Patent
Endo et al.

(10) Patent No.: US 10,758,554 B2
(45) Date of Patent: Sep. 1, 2020

(54) OPHTHALMIC AQUEOUS COMPOSITION

(71) Applicants: SANTEN PHARMACEUTICAL CO., LTD., Osaka-shi, Osaka (JP); DAIICHI SANKYO COMPANY, LIMITED, Chuo-ku, Tokyo (JP)

(72) Inventors: Yoko Endo, Ikoma (JP); Kyohei Takahashi, Ikoma (JP); Shinya Umezaki, Ikoma (JP)

(73) Assignees: SANTEN PHARMACEUTICAL CO., LTD., Osaka-Shi, Osaka (JP); DAIICHI SANKYO COMPANY, LIMITED, Chuo-Ku, Tokyo (JP)

( * ) Notice: Subject to any disclaimer, the term of this patent is extended or adjusted under 35 U.S.C. 154(b) by 0 days.

(21) Appl. No.: 15/523,970

(22) PCT Filed: Nov. 5, 2015

(86) PCT No.: PCT/JP2015/081121
§ 371 (c)(1),
(2) Date: May 3, 2017

(87) PCT Pub. No.: WO2016/072440
PCT Pub. Date: May 12, 2016

(65) Prior Publication Data
US 2017/0340644 A1 Nov. 30, 2017

(30) Foreign Application Priority Data
Nov. 7, 2014 (JP) ................. 2014-227039

(51) Int. Cl.
| | |
|---|---|
| *A61K 31/661* | (2006.01) |
| *A61K 31/573* | (2006.01) |
| *A61K 31/538* | (2006.01) |
| *A61K 9/00* | (2006.01) |
| *A61P 27/02* | (2006.01) |
| *A61K 47/10* | (2017.01) |
| *A61K 9/08* | (2006.01) |
| *A61K 31/5383* | (2006.01) |
| *A61K 47/02* | (2006.01) |
| *A61P 31/04* | (2006.01) |
| *A61P 29/00* | (2006.01) |
| *A61K 31/496* | (2006.01) |
| *C07J 5/00* | (2006.01) |
| *C07C 31/18* | (2006.01) |
| *C08G 65/00* | (2006.01) |

(52) U.S. Cl.
CPC .......... *A61K 31/661* (2013.01); *A61K 9/0048* (2013.01); *A61K 9/08* (2013.01); *A61K 31/496* (2013.01); *A61K 31/538* (2013.01); *A61K 31/5383* (2013.01); *A61K 31/573* (2013.01); *A61K 47/02* (2013.01); *A61K 47/10* (2013.01); *A61P 27/02* (2018.01); *A61P 29/00* (2018.01); *A61P 31/04* (2018.01); *C07J 5/0046* (2013.01); *C07C 31/18* (2013.01); *C08G 65/00* (2013.01)

(58) Field of Classification Search
CPC .. A61K 31/661; A61K 31/573; A61K 31/538; A61K 9/0048; A61P 27/02
See application file for complete search history.

(56) References Cited

U.S. PATENT DOCUMENTS

2001/0049366 A1* 12/2001 Singh .................. A61K 9/0043
514/171
2005/0009836 A1 1/2005 Laskar et al.

FOREIGN PATENT DOCUMENTS

| CN | 101199855 A | 6/2008 |
|---|---|---|
| JP | 2010254584 A * | 11/2010 |
| JP | 4758893 B2 | 8/2011 |
| SK | 500882014 U1 * | 11/2014 |
| SK | 500882014 U1 | 11/2014 |

OTHER PUBLICATIONS

Tahan et al. (Can J Surg, 54, 333-338, Oct. 2011) (Year: 2011).*
International Search Report (PCT/ISA/210) dated Jan. 26, 2016, by the Japanese Patent Office as the International Searching Authority for International Application No. PCT/JP2015/081121.
Written Opinion (PCT/ISA/237) dated Jan. 26, 2016, by the Japanese Patent Office as the International Searching Authority for International Application No. PCT/JP2015/081121.
Database WPI Section Ch, Week 200876 Thomson Scientific, London, GB; Class A96, AN 2008-M81927 Chen D; Chen L; Feng Y; Zhang Q: "Preparing cortex hormone inclusion compound water solution comprises adding clyclodextrin derivatives and cortex hormone into polar organic solvent, allowing it to dissolve, and evaporating organic solvent" (6 pages).
Extended Search Report issued by the European Patent Office in corresponding European Patent Application No. 15857116.6-1109 dated May 16, 2018 (8 pages).

* cited by examiner

*Primary Examiner* — Theodore R. West
(74) *Attorney, Agent, or Firm* — Buchanan Ingersoll & Rooney PC

(57) ABSTRACT

An ophthalmic aqueous composition comprises levofloxacin, a salt thereof, or a solvate thereof; dexamethasone, an ester thereof, or a salt thereof; and one or at least two isotonic agents. The ophthalmic aqueous composition is substantially free of sodium chloride. This ophthalmic aqueous composition is excellent in drug stability and drug migration and has a clear appearance.

16 Claims, No Drawings

OPHTHALMIC AQUEOUS COMPOSITION

TECHNICAL FIELD

The present invention relates to an ophthalmic aqueous composition comprising levofloxacin, a salt thereof, or a solvate thereof; dexamethasone, an ester thereof, or a salt thereof; and one or at least two isotonic agents, the ophthalmic aqueous composition being substantially free of sodium chloride.

BACKGROUND ART

Levofloxacin is known to inhibit bacterial DNA gyrase and topoisomerase IV to inhibit the DNA synthesis, exhibiting an antibacterial activity. Levofloxacin exhibits a broad antibacterial spectrum and a potent antibacterial action, and has already been widely used in the form of 0.5% (w/v) levofloxacin ophthalmic solution (Cravit(registered trademark) ophthalmic solution 0.5%). This ophthalmic solution contains levofloxacin as an active ingredient, as well as sodium chloride and a pH adjuster as additives. The ophthalmic solution is adjusted to have a pH of 6.2 to 6.8 and an osmotic pressure ratio of 1.0 to 1.1. The solution has a clear appearance.

Meanwhile, dexamethasone is a synthetic corticosteroid having a potent anti-inflammatory action. Among water-soluble ester derivatives thereof, particularly dexamethasone sodium phosphate has been widely used in the form of 0.1% (w/v) dexamethasone sodium phosphate ophthalmic solution (Orgadrone(registered trademark) ophthalmic solution 0.1%). This ophthalmic solution contains dexamethasone sodium phosphate as an active ingredient, as well as benzalkonium chloride, sodium edetate hydrate, boric acid, borax, and an isotonic agent as additives. The ophthalmic solution is adjusted to have a pH of 7.4 to 8.4 and be iso-osmotic. The solution has a clear appearance.

Generally, in making a drug in the form of an ophthalmic aqueous composition such as an ophthalmic solution, there are many problems to be solved, including drug stability, drug migration, and so on.

Patent Literature 1 states that blending levofloxacin at a concentration of 1.0 to 3.0% (w/v) with glycerin at such a concentration (2 to 2.5% (v/v)) as to render the composition substantially iso-osmotic enhances the efficacy of antimicrobial preservation.

However, there have been no known ophthalmic aqueous composition which contains levofloxacin, a salt thereof, or a solvate thereof and dexamethasone, an ester thereof, or a salt thereof, and which solves the problems with drug stability, drug migration, and so on.

CITATION LIST

Patent Literature

Patent Literature 1: Japanese Patent No. 4758893

SUMMARY OF INVENTION

An object of the present invention is to provide an ophthalmic aqueous composition comprising levofloxacin, a salt thereof, or a solvate thereof; and dexamethasone, an ester thereof, or a salt thereof, the ophthalmic aqueous composition being excellent in drug stability and/or drug migration and having a clear appearance.

The present inventors have earnestly studied the formulations of ophthalmic aqueous compositions containing levofloxacin, a salt thereof, or a solvate thereof; and dexamethasone, an ester thereof, or a salt thereof. As a result, the inventors have found out that incorporating one or at least two isotonic agents but substantially no sodium chloride makes a clear ophthalmic aqueous composition excellent in stability with suppressed insoluble deposit formation during the storage.

Further, the inventors have found out that adjusting the osmotic pressure ratio of such a composition to a low osmotic pressure, that is, adjusting the osmotic pressure ratio to 0.8 or less, enhances the drug migration of dexamethasone. These findings have led to the completion of the present invention.

Specifically, the present invention relates to the following.

(1) An ophthalmic aqueous composition comprising levofloxacin, a salt thereof, or a solvate thereof; dexamethasone, an ester thereof, or a salt thereof; and one or at least two isotonic agents, wherein the ophthalmic aqueous composition is substantially free of sodium chloride.

(2) The ophthalmic aqueous composition according to (1), wherein the ophthalmic aqueous composition has a pH of 6.5 to 8.8.

(3) The ophthalmic aqueous composition according to (1) or (2), wherein the ophthalmic aqueous composition has an osmotic pressure ratio of 1.2 or less.

(4) The ophthalmic aqueous composition according to (1) or (2), comprising the isotonic agent(s) at such a concentration as to adjust the osmotic pressure of the ophthalmic aqueous composition to a range of 60 to 340 mOsm.

(5) The ophthalmic aqueous composition according to any one of (1) to (3), comprising the isotonic agent(s) at such a concentration as to adjust the osmotic pressure of the ophthalmic aqueous composition to a range of 60 to 230 mOsm.

(6) The ophthalmic aqueous composition according to (1), wherein the isotonic agent(s) are a nonionic isotonic agent or an ionic isotonic agent.

(7) The ophthalmic aqueous composition according to (6), wherein the nonionic isotonic agent is a polyhydric alcohol.

(8) The ophthalmic aqueous composition according to (7), wherein the polyhydric alcohol is one or at least two selected from the group consisting of glycerin, propylene glycol, and polyethylene glycol.

(9) The ophthalmic aqueous composition according to (6), wherein the ionic isotonic agent is an inorganic salt.

(10) The ophthalmic aqueous composition according to (9), wherein the inorganic salt is boric acid or borax.

(11) The ophthalmic aqueous composition according to any one of (1) to (10), further comprising one or at least two thickening agents.

(12) An ophthalmic aqueous composition comprising levofloxacin, a salt thereof, or a solvate thereof at a concentration of 0.5% (w/v); dexamethasone, an ester thereof, or a salt thereof at a concentration of 0.1% (w/v); and glycerin at a concentration of 0.3 to 3.0% (w/v), wherein the ophthalmic aqueous composition is substantially free of sodium chloride, the ophthalmic aqueous composition has a pH of 6.5 to 8.8, and the ophthalmic aqueous composition has an osmotic pressure ratio of 0.3 to 1.2.

(13) The ophthalmic aqueous composition according to (12), further comprising benzalkonium chloride at a concentration of 0.001 to 0.02% (w/v).

(14) The ophthalmic aqueous composition according to (12) or (13), wherein the ophthalmic aqueous composition has an osmotic pressure ratio of 0.3 to 0.8.

(15) The ophthalmic aqueous composition according to any one of (1) to (14), which is an eye drop.

(16) The ophthalmic aqueous composition according to any one of (1) to (15), which is for preventing or treating an inflammatory disease of an outer ocular area or an anterior segment or a bacterial infection of an outer ocular area or an anterior segment.

(17) The ophthalmic aqueous composition according to (16), wherein the inflammatory disease of an outer ocular area or an anterior segment or the bacterial infection of an outer ocular area or an anterior segment is at least one selected from the group consisting of blepharitis, dacryocystitis, stye, conjunctivitis, allergic conjunctivitis, phlyctenular conjunctivitis, spring catarrh, tarsadenitis, keratitis, blepharokeratoconjunctivitis, superior limbic keratoconjunctivitis, filamentary keratitis, epidemic keratoconjunctivitis, corneal ulcer, scleritis, episcleritis, iritis, iridocyclitis, anterior uveitis, and postoperative inflammation.

(18) A method for suppressing insoluble deposit formation from an ophthalmic aqueous composition comprising levofloxacin, a salt thereof, or a solvate thereof; dexamethasone, an ester thereof, or a salt thereof; and one or at least two isotonic agents, the ophthalmic aqueous composition being substantially free of sodium chloride.

(19) The method according to (18), wherein the ophthalmic aqueous composition has a pH of 6.5 to 8.8.

Note that any of one or more configurations (1) to (19) above can be selected in combination.

According to the present invention, the ophthalmic aqueous composition comprises levofloxacin, a salt thereof, or a solvate thereof; dexamethasone, an ester thereof, or a salt thereof; and one or at least two isotonic agents, but the ophthalmic aqueous composition is substantially free of sodium chloride. This makes it possible to provide a clear ophthalmic aqueous composition excellent in stability with suppressed insoluble deposit formation during the storage.

Moreover, it is possible to provide a clear ophthalmic aqueous composition with enhanced drug migration of dexamethasone by making the osmotic pressure ratio of the composition to 0.8 or less.

Further, the composition is useful against inflammatory diseases of an outer ocular area or an anterior segment or bacterial infections of an outer ocular area or an anterior segment, such as blepharitis, dacryocystitis, stye, conjunctivitis, allergic conjunctivitis, phlyctenular conjunctivitis, spring catarrh, tarsadenitis, keratitis, blepharokeratoconjunctivitis, superior limbic keratoconjunctivitis, filamentary keratitis, epidemic keratoconjunctivitis, corneal ulcer, scleritis, episcleritis, iritis, iridocyclitis, anterior uveitis, and postoperative inflammation.

DESCRIPTION OF EMBODIMENTS

Hereinafter, embodiments of the present invention will be described. However, the present invention is not limited thereto.

Levofloxacin is a compound represented by the following chemical structural formula (I).

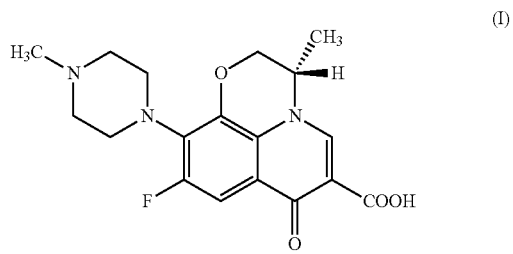 [SMILES: C[C@H]1COc2c(N3CCN(C)CC3)c(F)cc3c(=O)c(C(=O)O)cn1c23]

A salt of levofloxacin is not particularly limited, as long as it is a pharmaceutically acceptable salt. Examples thereof include salts with an inorganic acid such as hydrochloric acid, hydrobromic acid, hydroiodic acid, nitric acid, sulfuric acid, or phosphoric acid; salts with an organic acid such as acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, sulfuric acid lauryl ester, methyl sulfate, naphthalenesulfonic acid, or sulfosalicylic acid; quaternary ammonium salts with methyl bromide, methyl iodide, or the like; salts with a halogen ion such as a bromine ion, a chlorine ion, or an iodine ion; salts with an alkali metal such as lithium, sodium, or potassium; salts with an alkaline earth metal such as calcium or magnesium; salts with a metal such as iron or zinc; salts with ammonia; salts with an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine, or N,N-bis(phenylmethyl)-1,2-ethanediamine; and the like.

In a case where levofloxacin, a salt thereof, or a solvate thereof undergoes proton tautomerization, the tautomers are also included in the scope of the present invention.

A solvate of levofloxacin or a salt thereof is not particularly limited, as long as it is a pharmaceutically acceptable solvate. Examples thereof include hydrates (such as hemihydrates, monohydrates, dihydrates), organic solvates, and the like. Preferable are hydrates (hemihydrates, monohydrates, or dihydrates), and more preferable are hemihydrates.

In a case where levofloxacin, a salt thereof, or a solvate thereof exhibits polymorphism and a polymorphic group (polymorphic system) exists, the polymorphs and the polymorphic group (polymorphic system) are also included in the scope of the present invention. Here, the polymorphic group (polymorphic system) means the crystal form in each stage in a case where the crystal form changes according to the conditions in production, crystallization, storage, and the like of the crystal, and to the state (note that this state also includes a state of being prepared into a pharmaceutical preparation), as well as the entire process.

Levofloxacin, a salt thereof, or a solvate thereof can be produced according to the methods described in Japanese Examined Patent Application Publication Nos. Hei 3-27534 and Hei 7-47592. Additionally, in the present invention, commercially-available levofloxacin hydrochloride (e.g., manufactured by Wako Pure Chemical Industries, Ltd.; distributor code: 121-05943) and the like can also be used.

The content of levofloxacin, a salt thereof, or a solvate thereof is not particularly limited, as long as the content is sufficient to exhibit a desired efficacy. The content can be adjusted as appropriate depending on: the disease to be treated and the symptom; the age and body weight of a patient; the content of dexamethasone, an ester thereof, or a salt thereof, which is one active ingredient of the ophthalmic aqueous composition according to the present invention; the content of the other additive(s); the osmotic pressure (osmotic pressure ratio) of the ophthalmic aqueous composition; and so forth. The content of levofloxacin, a salt thereof, or a solvate thereof is for example 0.3 to 5% (w/v), preferably 0.3 to 3% (w/v), more preferably 0.3 to 1.5% (w/v), and particularly preferably 0.5 to 1.5% (w/v).

Dexamethasone is a compound represented by the following chemical structural formula (IIa).

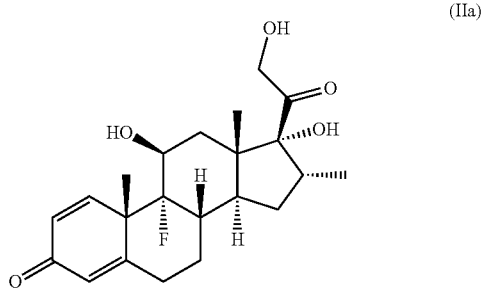

(IIa)

An ester of dexamethasone is not particularly limited, as long as it is a pharmaceutically acceptable ester. Examples thereof include dexamethasone acetate, dexamethasone propionate, dexamethasone valerate, dexamethasone palmitate, dexamethasone metasulfobenzoate, dexamethasone cipecilate, dexamethasone phosphate, and the like. Preferable is dexamethasone phosphate.

A salt of dexamethasone or an ester thereof is not particularly limited, as long as it is a pharmaceutically acceptable salt. Examples thereof include salts with an inorganic acid such as hydrochloric acid, hydrobromic acid, hydroiodic acid, nitric acid, sulfuric acid, or phosphoric acid; salts with an organic acid such as acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, sulfuric acid lauryl ester, methyl sulfate, naphthalenesulfonic acid, or sulfosalicylic acid; quaternary ammonium salts with methyl bromide, methyl iodide, or the like; salts with a halogen ion such as a bromine ion, a chlorine ion, or an iodine ion; salts with an alkali metal such as lithium, sodium, or potassium; salts with an alkaline earth metal such as calcium or magnesium; salts with a metal such as iron or zinc; salts with ammonia; salts with an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine, or N,N-bis(phenylmethyl)-1,2-ethanediamine; and the like. Preferable are salts with an alkali metal, and more preferable is a salt with sodium.

Among dexamethasone, esters thereof, and salts thereof in the present invention, dexamethasone sodium phosphate is a compound represented by the following chemical structural formula (IIb).

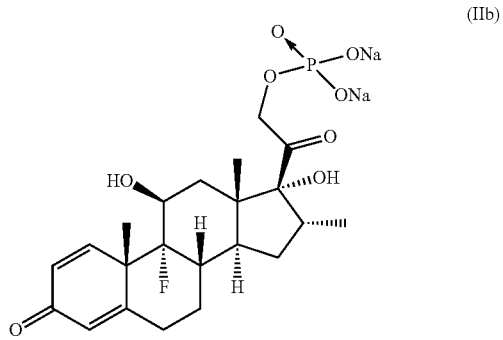

(IIb)

In a case where dexamethasone, an ester thereof, or a salt thereof undergoes proton tautomerization, the tautomers are also included in the scope of the present invention.

In a case where a solvate exists in dexamethasone, an ester thereof, or a salt thereof, such solvates are also included in the scope of the present invention. The solvate of dexamethasone, an ester thereof, or a salt thereof is not particularly limited, as long as it is a pharmaceutically acceptable solvate. Examples thereof include hydrates (such as hemihydrates, monohydrates, dihydrates), organic solvates, and the like.

In a case where dexamethasone, an ester thereof, or a salt thereof exhibits polymorphism and a polymorphic group (polymorphic system) exists, the polymorphs and the polymorphic group (polymorphic system) are also included in the scope of the present invention. Here, the polymorphic group (polymorphic system) means the crystal form in each stage in a case where the crystal form changes according to the conditions in production, crystallization, storage, and the like of the crystal, and to the state (note that this state also includes a state of being prepared into a pharmaceutical preparation), as well as the entire process.

Dexamethasone, an ester thereof, or a salt thereof can be produced by a normal method in the field of synthetic organic chemistry. Moreover, in the present invention, commercially-available products can also be used. For example, dexamethasone sodium phosphate manufactured by Wako Pure Chemical Industries, Ltd. (distributor code: 554-74381) and the like can also be used.

Further, the content of dexamethasone, an ester thereof, or a salt thereof in the present invention is not particularly limited, as long as the content is sufficient to exhibit a desired efficacy. The content can be adjusted as appropriate depending on: the disease to be treated and the symptom; the age and body weight of a patient; the content of levofloxacin, a salt thereof, or a solvate thereof, which is one active ingredient of the ophthalmic aqueous composition according to the present invention; the content of the other additive(s); the osmotic pressure (osmotic pressure ratio) of the ophthalmic aqueous composition; and so forth. The content of dexamethasone, an ester thereof, or a salt thereof is for example 0.01 to 0.3% (w/v), preferably 0.025 to 0.2%, more preferably 0.05 to 0.12% (w/v), and particularly preferably 0.10 to 0.12% (w/v).

Furthermore, in a case where dexamethasone, an ester thereof, or a salt thereof in the present invention is dexamethasone phosphoric acid ester or salt also, the content is not particularly limited, as long as the content is sufficient to exhibit a desired efficacy. The content can be adjusted as appropriate depending on: the disease to be treated and the symptom; the age and body weight of a patient; the content of levofloxacin, a salt thereof, or a solvate thereof, which is one active ingredient of the ophthalmic aqueous composition according to the present invention; the content of the other additive(s); the osmotic pressure (osmotic pressure ratio) of the ophthalmic aqueous composition; and so forth. The content of the dexamethasone phosphoric acid ester or salt is for example 0.01 to 0.3% (w/v), preferably 0.025 to 0.2%, more preferably 0.05 to 0.12% (w/v), and particularly preferably 0.10 to 0.12% (w/v).

In the present invention, an isotonic agent is not particularly limited, as long as it is a pharmaceutically acceptable isotonic agent. Examples thereof include ionic isotonic agents, nonionic isotonic agents, and the like.

Examples of the ionic isotonic agents include inorganic salts and organic salts.

Examples of the inorganic salts include disodium phosphate, sodium dihydrogen phosphate, potassium dihydrogen phosphate, sodium hydrogen sulfite, sodium sulfite, sodium thiosulfate, magnesium sulfate, sodium chloride, potassium chloride, calcium chloride, magnesium chloride, boric acid, borax, and the like.

Examples of the organic salts include potassium acetate, sodium acetate, sodium hydrogen carbonate, sodium carbonate, and the like.

Examples of the nonionic isotonic agents include polyhydric alcohols having two or more alcoholic hydroxy groups in single molecules, and the like.

Specific examples of the polyhydric alcohols include, for example, glycerin, propylene glycol, polyethylene glycol, glucose, trehalose, sucrose, xylitol, sorbitol, and the like.

Among these isotonic agents, the nonionic isotonic agents are preferably polyhydric alcohols such as glycerin, propylene glycol, and polyethylene glycol; the ionic isotonic agents are preferably inorganic salts such as boric acid and borax; more preferable are glycerin and borax; particularly preferable is glycerin.

Moreover, one of the isotonic agents in the present invention may be used alone, or two or more thereof may be used in any combination.

Further, the concentration of the isotonic agent in the present invention can be adjusted as appropriate in consideration of: the influence on the drug and/or the other additive(s); and the adjustment of the osmotic pressure (osmotic pressure ratio) of the ophthalmic aqueous composition to a particular range. In the case where the isotonic agent in the present invention is a nonionic isotonic agent, the concentration is for example 10 to 1000 mmol/L, preferably 20 to 500 mmol/L, more preferably 20 to 300 mmol/L, and particularly preferably 20 to 200 mmol/L. In the case of an ionic isotonic agent, the concentration of all ions including cations and anions but not those of the drug is 10 to 1000 (mmol/L), preferably 20 to 500 (mmol/L), more preferably 20 to 300 (mmol/L), and particularly preferably 20 to 200 (mmol/L).

Furthermore, in the case where the isotonic agent in the present invention is a nonionic isotonic agent or a polyhydric alcohol, particularly glycerin, the content can be adjusted as appropriate in consideration of the influence on the drug, the other additive(s), and/or the osmotic pressure (osmotic pressure ratio) of the ophthalmic aqueous composition. The content of a nonionic isotonic agent or a polyhydric alcohol, particularly glycerin (the molecular weight: 92.09), in the present invention is for example 0.01 to 10% (w/v), preferably 0.05 to 5% (w/v), more preferably 0.1 to 3.0% (w/v), furthermore preferably 0.3 to 3.0% (w/v), and particularly preferably 0.3 to 1.9% (w/v).

The ophthalmic aqueous composition according to the present invention is substantially free of sodium chloride. Here, the phrase "substantially free of" means that the content does not adversely influence the stability, for example, physical stability, of the ophthalmic aqueous composition. Specifically, the content of sodium chloride is for example less than 0.6% (w/v), preferably 0.5% (w/v) or less, 0.4% (w/v) or less, or 0.3% (w/v) or less, more preferably 0.27% (w/v) or less, furthermore preferably 0.2% (w/v) or less, still furthermore preferably 0.18% (w/v) or less, and particularly preferably 0.14% (w/v) or less.

The pH of the ophthalmic aqueous composition according to the present invention is not particularly limited, as long as it is within a pharmaceutically acceptable range. For example, the pH is within a range of 4.0 to 9.0, preferably 4.0 to 8.8, and more preferably 6.5 to 8.8.

The ophthalmic aqueous composition according to the present invention can be blended as necessary with a base. The base is not particularly limited, as long as it is a pharmaceutically acceptable base. Examples thereof can include sodium hydroxide, potassium hydroxide, monoethanolamine, diethanolamine, triethanolamine, trometamol, meglumine, and the like.

In addition, the ophthalmic aqueous composition according to the present invention can also be blended as necessary with an acid such as an organic acid or an inorganic acid.

Moreover, one of these pH adjusters may be used alone, or two or more thereof may be used in any combination.

The osmotic pressure ratio of the ophthalmic aqueous composition according to the present invention means an osmotic pressure ratio of the composition to saline. Note that the value can be measured by a usual method. For example, the measurement is possible according to the method described in the section of osmotic pressure measurement method (Osmolarity Determination) in The Japanese Pharmacopoeia, Fifteenth Edition.

Moreover, the osmotic pressure ratio of the ophthalmic aqueous composition according to the present invention is not particularly limited, as long as it is within a range acceptable to the living body. The osmotic pressure ratio is for example 0.01 to 3.5, preferably 0.01 to 2.0, more preferably 0.1 to 1.5, furthermore preferably 0.3 to 1.2, and particularly preferably 0.3 to 0.8.

Generally, the osmotic pressure ratio of an aqueous composition is influenced greatly to some extent by the contents of a drug and an additive contained in the aqueous composition. In the present invention, the osmotic pressure ratio can be adjusted to the above-described ranges by adjusting as appropriate the content of each substance that may influence the osmotic pressure.

Further, the osmotic pressure of the ophthalmic aqueous composition according to the present invention is not particularly limited, as long as it is within a range acceptable to the living body. The osmotic pressure is for example 10 to 1000 mOsm, preferably 30 to 500 mOsm, more preferably 60 to 340 mOsm, furthermore preferably 60 to 260 mOsm, and particularly preferably 60 to 230 mOsm.

The ophthalmic aqueous composition according to the present invention can be further blended with one or at least two thickening agents without particular limitation, as long as the thickening agent(s) are pharmaceutically acceptable.

Examples of the thickening agent in the present invention include cellulose polymers (such as methyl cellulose, ethyl cellulose, hydroxyethyl cellulose, hydroxypropylmethyl cellulose), vinyl polymers (such as polyvinylpyrrolidone), sugars (mucopolysaccharides such as hyaluronic acid and salts thereof; polysaccharides such as gellan gum, sodium alginate, dextran, cyclodextrin), oxyalkylene polymers (polyoxyethylene-polyoxypropylene block copolymers), and the like.

The molecular weight of the thickening agent in the present invention can be selected, for example, from a range of approximately $0.5 \times 10^4$ to $100 \times 10^4$ as the number average molecular weight.

Moreover, the content of the thickening agent in the present invention can be adjusted as appropriate in consideration of the influence on the drug, the other additive(s), and/or the osmotic pressure (osmotic pressure ratio). The content of the thickening agent in the present invention is for example 0.001 to 10% (w/v), preferably 0.01 to 5% (w/v), more preferably 0.03 to 3% (w/v), furthermore preferably 0.05 to 2.5% (w/v), and particularly preferably 0.1 to 2.0% (w/v).

The ophthalmic aqueous composition according to the present invention can be blended as necessary with a nonionic surfactant. The nonionic surfactant is not particularly limited, as long as it is within a pharmaceutically acceptable range. Examples thereof include polyoxyethylene fatty acid esters, polyoxyethylene sorbitan fatty acid esters, polyoxyethylene castor oil derivatives, polyoxyethylene polyoxypropylene glycols, sucrose fatty acid esters, and the like. The polyoxyethylene fatty acid esters include polyoxyl 40 stearate, and the like. The polyoxyethylene sorbitan fatty acid esters include polysorbate 80, polysorbate 60, polysorbate 40, polyoxyethylene sorbitan monolaurate, polyoxyethylene sorbitan trioleate, polysorbate 65, and the like. The polyoxyethylene castor oil derivatives include polyoxyethylene hydrogenated castor oil 10, polyoxyethylene hydrogenated castor oil 40, polyoxyethylene hydrogenated castor oil 50, polyoxyethylene hydrogenated castor oil 60, polyoxyl 5 castor oil, polyoxyl 9 castor oil, polyoxyl 15 castor oil, polyoxyl 35 castor oil, polyoxyl 40 castor oil, and the like. The polyoxyethylene polyoxypropylene glycols include polyoxyethylene (160) polyoxypropylene (30) glycol, polyoxyethylene (42) polyoxypropylene (67) glycol, polyoxyethylene (54) polyoxypropylene (39) glycol, polyoxyethylene (196) polyoxypropylene (67) glycol, polyoxyethylene (20) polyoxypropylene (20) glycol, and the like.

Moreover, one of these nonionic surfactants may be used alone, or two or more thereof may be used in any combination.

The ophthalmic aqueous composition according to the present invention can be blended as necessary with a buffer. The buffer is not particularly limited, as long as it is within a pharmaceutically acceptable range. Examples thereof include phosphoric acid or salts thereof, boric acid or salts thereof, citric acid or salts thereof, acetic acid or salts thereof, carbonic acid or salts thereof, tartaric acid or salts thereof, ε-aminocaproic acid, trometamol, and the like. The phosphoric acid salts include sodium phosphate, sodium dihydrogen phosphate, disodium phosphate, potassium phosphate, potassium dihydrogen phosphate, dipotassium hydrogen phosphate, and the like. The boric acid salts include borax, sodium borate, potassium borate, and the like. The citric acid salts include sodium citrate, disodium citrate, and the like. The acetic acid salts include sodium acetate, potassium acetate, and the like. The carbonic acid salts include sodium carbonate, sodium hydrogen carbonate, and the like. The tartaric acid salts include sodium tartrate, potassium tartrate, and the like.

Moreover, one of these buffers may be used alone, or two or more thereof may be used in any combination.

The ophthalmic aqueous composition according to the present invention can be blended as necessary with a stabilizer. The stabilizer is not particularly limited, as long as it is within a pharmaceutically acceptable range. Examples thereof include edetic acid, sodium edetate, and the like.

Moreover, one of these stabilizers may be used alone, or two or more thereof may be used in any combination.

The ophthalmic aqueous composition according to the present invention can be blended as necessary with a preservative usable as an additive of a pharmaceutical drug. The preservative is not particularly limited, as long as it is within a pharmaceutically acceptable range. Examples thereof include sorbic acid, potassium sorbate, benzalkonium chloride, benzethonium chloride, methyl paraoxybenzoate, propyl paraoxybenzoate, chlorobutanol, boric acid, borax, and the like.

Moreover, one of these preservatives may be used alone, or two or more thereof may be used in any combination.

Further, the content of the preservative in the present invention can be adjusted as appropriate in consideration of the influence on the drug, the other additive(s), and/or the osmotic pressure (osmotic pressure ratio). The content of the preservative in the present invention is for example 0.001 to 0.02% (w/v), preferably 0.001 to 0.01% (w/v), and more preferably 0.001 to 0.005% (w/v).

In the present invention, the term "aqueous composition" means a composition having water as a base.

In the present invention, the term "ophthalmic aqueous composition" means an aqueous composition used in an ophthalmic topical administration. In the "ophthalmic aqueous composition" in the present invention, more than 80% (w/v) of the composition is water, and preferably more than 90% (w/v) of the composition is water.

Examples of the dosage form of the ophthalmic aqueous composition according to the present invention can include an ophthalmic injection and an eye drop, and the dosage form is preferably an eye drop.

The ophthalmic aqueous composition according to the present invention has a sufficient stability for use as a pharmaceutical drug.

The disease against which the ophthalmic aqueous composition according to the present invention is applicable is not particularly limited. Examples thereof can include inflammatory diseases of an outer ocular area or an anterior segment or bacterial infections of an outer ocular area or an anterior segment, such as blepharitis, dacryocystitis, stye, conjunctivitis, allergic conjunctivitis, phlyctenular conjunctivitis, spring catarrh, tarsadenitis, keratitis, blepharokeratoconjunctivitis, superior limbic keratoconjunctivitis, filamentary keratitis, epidemic keratoconjunctivitis, corneal ulcer, scleritis, episcleritis, iritis, iridocyclitis, anterior uveitis, and postoperative inflammation.

The number of administrations of the ophthalmic aqueous composition according to the present invention is not particularly limited, as long as it is sufficient to exhibit a desired efficacy. The number can be selected as appropriate depending on: the disease to be treated and the symptom; and the age and body weight of a patient. For example, the instillation is possible at a dose of 1 to several drops (for example, 1 to 3 drops, preferably 1 drop) once to several times (for example, 1 to 6 times) per day.

As the method for preparing the ophthalmic aqueous composition according to the present invention, the composition can be prepared by generally used methods.

In the present invention, the term "clear" means that the target composition is transparent when a glass container (such as glass vial, glass ampoule) is filled with the composition and visually checked.

EXAMPLES

Hereinafter, the results of test examples will be described. However, these examples are for better understanding of the present invention, and are not to limit the scope of the present invention.

[Test Example 1] Physical Stability Test

Whether the appearance of the ophthalmic aqueous composition according to the present invention changed or not during the storage was visually checked to evaluate the physical stability.

(Sample Preparation)

Example 1

According to the formulation shown in Table 1, an ophthalmic solution of Example 1 was prepared. Specifically, 0.5 g of levofloxacin hemihydrate, 0.1 g of dexamethasone sodium phosphate, and 2.5 g of glycerin were dissolved in purified water. A sodium hydroxide solution was added thereto to adjust the pH to 7.0. The whole amount was made 100 mL.

Examples 2 to 9, Comparative Examples 1 to 3, and Reference Example 1

According to the formulations shown in Table 1, ophthalmic solutions of Examples 2 to 9, Comparative Examples 1 to 3, and Reference Example 1 were prepared in the same manner as in Example 1.

(Test Method)

A colorless, transparent plastic container (5 mL) was filled with one of the ophthalmic solutions of Examples 1 to 9, Comparative Examples 1 to 3, and Reference Example 1. Whether the appearance changed or not was visually checked immediately after the preparation or after the storage at room temperature or 60° C. for 7 days, to evaluate the physical stability. O indicates a case where no insoluble deposit was observed, resulting in a clear solution. X indicates a case where an insoluble deposit was observed, resulting in an unclear solution.

(Test Result)

Table 1 shows the test result.

TABLE 1

(Unit: g/100 mL)

| | | Example | | | | | | | | Comparative Example | | | Reference Example |
|---|---|---|---|---|---|---|---|---|---|---|---|---|---|
| | | 1 | 2 | 3 | 4 | 5 | 6 | 7 | 8 | 9 | 1 | 2 | 3 | 1 |
| levofloxacin hemihydrate | | 0.5 | 0.5 | 0.5 | 0.5 | 0.5 | 0.5 | 0.5 | 0.5 | 0.5 | 0.5 | 0.5 | 0.5 | — |
| dexamethasone sodium phoshate | | 0.1 | 0.1 | 0.1 | 0.1 | 0.1 | 0.1 | 0.1 | 0.1 | 0.1 | 0.1 | 0.1 | 0.1 | 0.1 |
| glycerin[*1] | | 2.5 | 2.5 | 2.5 | 1.3 | 2.5 | — | — | — | 1.3 | — | — | — | — |
| propylene glycol[*2] | | — | — | — | — | — | 1.9 | 0.27 | 0.14 | — | 0.9 | 0.9 | 0.6 | — |
| sodium chloride | | — | — | — | — | — | — | — | — | — | — | — | — | — |
| sodium edetate hydrate | | — | — | 0.5 | — | — | — | — | — | — | — | — | — | — |
| benzalkonium chloride | | — | — | — | — | — | — | — | — | 0.005 | — | — | — | — |
| sodium hydroxide | | q.s. | q.s. | q.s. | q.s. | q.s. | q.s. | q.s. | q.s. | q.s. | q.s. | q.s. | q.s. | q.s. |
| purified water | | q.s. | q.s. | q.s. | q.s. | q.s. | q.s. | q.s. | q.s. | q.s. | q.s. | q.s. | q.s. | q.s. |
| pH | | 7.0 | 8.0 | 8.0 | 8.0 | 8.5 | 8.0 | 8.5 | 8.5 | 8.0 | 8.0 | 8.5 | 8.5 | 8.0 |
| osmotic pressure (mOsm) | | 298 | 311 | 304 | 166 | 308 | 286 | 112 | 72 | 165 | not measured | 316 | 221 | not measured |
| osmotic pressure ratio | | 1.0 | 1.1 | 1.1 | 0.6 | 1.1 | 1.0 | 0.4 | 0.3 | 0.6 | 1.0 | 1.1 | 0.8 | 1.0 |
| Result | immediately after the preparation | ○ | ○ | ○ | ○ | ○ | ○ | ○ | ○ | ○ | ○ | ○ | ○ | ○ |
| | room temperature, 7 days later | ○ | ○ | ○ | ○ | ○ | ○ | ○ | ○ | ○ | ○ | ○ | ○ | ○ |
| | 60° C., 7 days later | ○ | ○ | ○ | ○ | ○ | ○ | ○ | ○ | ○ | x | x | x | ○ |

TABLE 1-continued (Unit: g/100 mL)

| | | | | | | |
|---|---|---|---|---|---|---|
| ○ | ○ | ○ | x | x | x | ○ |
| ○ | ○ | ○ | x | x | not measured | not measured |

*¹gylcerin has a molecular weight of 92.09.
*²propylene glycol has a molecular weight of 76.09.
q.s. means appropriate amount The result in Test Example 1 showed that the ophthalmic aqueous compositions were clear solutions with suppressed insoluble deposit formation, the ophthalmic aqueous compositions each containing: levofloxacin, a salt thereof, or a solvate thereof; dexamethasone, an ester thereof, or a salt thereof; an isotonic agent; and substantially no sodium chloride.

[Test Example 2] Thermal Stability Test

The thermal stabilities of levofloxacin hemihydrate and dexamethasone sodium phosphate in the ophthalmic aqueous compositions according to the present invention were examined.
(Sample Preparation)

Example 4

According to the formulation shown in Table 1, an ophthalmic solution of Example 4 was prepared in the same manner as in Test Example 1.
(Test Method)
The ophthalmic solution of Example 4 was stored at 40° C. for two weeks and one month or at 25° C. for one month. Then, the contents of levofloxacin and dexamethasone sodium phosphate in the ophthalmic solution were quantified by using high-performance liquid chromatography (HPLC) to calculate the residual ratios.
(Test Result)
Table 2 shows the test result.

TABLE 2

| | | Example 4 | | |
|---|---|---|---|---|
| Storage conditions | | 40° C., 2 weeks | 40° C., 1 month | 25° C., 1 month |
| residual ratio (%) | levofloxacin hemihydrate | 101 | 101 | 101 |
| | dexamethasone sodium phosphate | 100 | 100 | 100 |

As is apparent from Table 2, the ophthalmic solution of Example 4 exhibited a stable result after two weeks and one month at 40° C. or after one month at 25° C. Note that, before and after the test, no insoluble deposit was observed, and the ophthalmic solution was a clear solution.

[Test Example 3] Drug Migration Test

The migration of dexamethasone in aqueous humor was examined using the ophthalmic aqueous compositions according to the present invention.
(Sample Preparation)

Examples 4, 9 to 16

According to the formulations shown in Table 3, ophthalmic solutions of Examples 4, 9 to 16 were prepared in the same manner as in Test Example 1.
(Test Method)
The dexamethasone concentration in the aqueous humor was measured by the LC-MS/MS method when the ophthalmic solutions of Examples 4, 9 to 16 were each instilled into eyes of JW male white rabbits once.
(Administration Method and Measurement Method)
1) With MICROMAN, 50 μL of one of the ophthalmic solutions was instilled onto the corneas.
2) While the rabbits were each put in a holder for a predetermined period under non-anesthesia, a pentobarbital preparation (product name: Somnopentyl injection) was injected into the auricular vein for euthanasia.
3) After the eyeballs were washed with a saline, the aqueous humor was collected.
4) A pretreatment was performed using 50 μL of the collected aqueous humor per eye, and the dexamethasone concentration in the aqueous humor was then measured by the LC-MS/MS method.
(Test Result)
Table 3 snows the dexamethasone concentrations (Cmax, average values of four or six eyes) in the aqueous humor.

TABLE 3

(Unit: g/100 mL)

| | Example | | | | | | | | |
|---|---|---|---|---|---|---|---|---|---|
| | 9 | 10 | 11 | 4 | 12 | 13 | 14 | 15 | 16 |
| levofloxacin hemihydrate | 0.5 | 0.5 | 0.5 | 0.5 | 0.5 | 0.5 | 0.5 | 0.5 | 0.5 |
| dexamethasone sodium phosphate | 0.1 | 0.1 | 0.1 | 0.1 | 0.1 | 0.1 | 0.1 | 0.1 | 0.1 |
| glycerin | 1.3 | 2.3 | 2.3 | 1.3 | 0.46 | 2.3 | 0.5 | 0.5 | — |
| borax | — | — | — | — | — | — | — | — | 1.0 |
| hydroxyethyl cellulose | — | — | — | — | — | 0.2 | — | — | — |

TABLE 3-continued (Unit: g/100 mL)

| | Example | | | | | | | | |
|---|---|---|---|---|---|---|---|---|---|
| | 9 | 10 | 11 | 4 | 12 | 13 | 14 | 15 | 16 |
| gellan gum | — | — | — | — | — | — | 0.6 | — | — |
| sodium alginate | — | — | — | — | — | — | — | 0.3 | — |
| benzalkonium chloride | 0.005 | — | — | — | — | — | — | — | — |
| trometamol | — | — | — | — | — | — | q.s. | — | — |
| sodium hydroxide | q.s. | q.s. | q.s. | q.s. | q.s. | q.s. | — | q.s. | q.s. |
| purified water | q.s. | q.s. | q.s. | q.s. | q.s. | q.s. | q.s. | q.s. | q.s. |
| pH | 8.0 | 8.8 | 8.3 | 8.0 | 8.3 | 8.3 | 8.3 | 8.3 | 8.3 |
| osmotic pressure (mOsm) | 165 | 289 | 283 | 170 | 74 | 283 | 93 | 83 | 185 |
| osmotic pressure | 0.6 | 1.0 | 1.0 | 0.6 | 0.3 | 1.0 | 0.3 | 0.3 | 0.6 |
| dexamethasone concentration Cmax (mg/mL) in aqueous humor | 73.5 | 62.7 | 64.8 | 76.8 | 76.4 | 106.5 | 82.9 | 83.7 | 96.1 |

As shown in Table 3, the ophthalmic solutions of Examples 4, 9 to 16 exhibited high dexamethasone mobilities in the aqueous humor.

INDUSTRIAL APPLICABILITY

The ophthalmic aqueous composition according to the present invention is a clear solution excellent in drug stability and drug migration. Moreover, the composition is useful against inflammatory diseases of an outer ocular area or an anterior segment or bacterial infections of an outer ocular area or an anterior segment.

What is claimed is:

1. An ophthalmic aqueous composition consisting of levofloxacin, a salt thereof, or a solvate thereof; phosphate ester of dexamethasone or a salt thereof as active ingredients and one or at least two isotonic agents; and benzalkonium chloride as additives; and optionally containing a buffer and a pH adjuster, wherein the ophthalmic aqueous composition is substantially free of sodium chloride and has a pH of 6.5 to 8.8.

2. The ophthalmic aqueous composition according to claim 1, wherein the ophthalmic aqueous composition has an osmotic pressure ratio of 1.2 or less.

3. The ophthalmic aqueous composition according to claim 1, comprising the isotonic agent(s) at such a concentration as to adjust the osmotic pressure of the ophthalmic aqueous composition to a range of 60 to 340 mOsm.

4. The ophthalmic aqueous composition according to claim 1, comprising the isotonic agent(s) at such a concentration as to adjust the osmotic pressure of the ophthalmic aqueous composition to a range of 60 to 230 mOsm.

5. The ophthalmic aqueous composition according to claim 1, wherein the isotonic agent(s) are a nonionic isotonic agent or an ionic isotonic agent.

6. The ophthalmic aqueous composition according to claim 5, wherein the nonionic isotonic agent is a polyhydric alcohol.

7. The ophthalmic aqueous composition according to claim 6, wherein the polyhydric alcohol is one or at least two selected from the group consisting of glycerin, propylene glycol, and polyethylene glycol.

8. The ophthalmic aqueous composition according to claim 5, wherein the ionic isotonic agent is an inorganic salt.

9. The ophthalmic aqueous composition according to claim 8, wherein the inorganic salt is boric acid or borax.

10. The ophthalmic aqueous composition according to claim 5, wherein the ionic isotonic agent is selected from the group consisting of inorganic salts and organic salts.

11. The ophthalmic aqueous composition according to claim 5, wherein the ionic isotonic agent comprises an inorganic salt.

12. The ophthalmic aqueous composition according to claim 1, which is an eye drop.

13. An ophthalmic aqueous composition according to claim 1, which contains a buffer and a pH adjuster.

14. An ophthalmic aqueous composition consisting of levofloxacin, a salt thereof, or a solvate thereof at a concentration of 0.5% to 1.5% (w/v); phosphate ester of dexamethasone or a salt thereof at a concentration of 0.025 to 0.2% (w/v); one or at least two isotonic agents; benzalkonium chloride at a concentration of 0.001 to 0.02% (w/v); a buffer; a pH adjuster; and water, wherein the ophthalmic aqueous composition is substantially free of sodium chloride,
the ophthalmic aqueous composition has a pH of 6.5 to 8.8, and
the ophthalmic aqueous composition has an osmotic pressure ratio of 0.3 to 1.2.

15. The ophthalmic aqueous composition according to claim 14, wherein the ophthalmic aqueous composition has an osmotic pressure ratio of 0.3 to 0.8.

16. An ophthalmic aqueous composition consisting of levofloxacin, a salt thereof, or a solvate thereof; phosphate ester of dexamethasone or a salt thereof; one or at least two isotonic agents; benzalkonium chloride; a buffer; a pH adjuster; and water wherein the ophthalmic aqueous composition is substantially free of sodium chloride and has a pH of 6.5 to 8.8.

* * * * *